United States Patent
Yang et al.

(10) Patent No.: US 11,590,115 B2
(45) Date of Patent: Feb. 28, 2023

(54) *PSEUDOMONAS* STRAINS AND THEIR METABOLITES TO CONTROL FISH DISEASES

(71) Applicants: T3 BIOSCIENCE, LLC, Mequon, WI (US); UWM RESEARCH FOUNDATION, INC., Milwaukee, WI (US)

(72) Inventors: Ching-Hong Yang, Mequon, WI (US); Jian Huang, Milwaukee, WI (US)

(73) Assignees: T3 BIOSCIENCE, LLC, Mequon, WI (US); UWM RESEARCH FOUNDATION, INC., Milwaukee, WI (US)

( * ) Notice: Subject to any disclaimer, the term of this patent is extended or adjusted under 35 U.S.C. 154(b) by 0 days.

(21) Appl. No.: 17/494,068

(22) Filed: Oct. 5, 2021

(65) Prior Publication Data
US 2022/0105080 A1 Apr. 7, 2022

Related U.S. Application Data

(63) Continuation-in-part of application No. PCT/US2021/053405, filed on Oct. 4, 2021, and a continuation-in-part of application No. 17/493,594, filed on Oct. 4, 2021, and a continuation-in-part of application No. PCT/US2020/054303, filed on Oct. 5, 2020, and a continuation-in-part of application No. 17/063,540, filed on Oct. 5, 2020.

(30) Foreign Application Priority Data

Oct. 5, 2020 (AR) .............................. P 20 01 02757
Oct. 5, 2020 (TW) .................................. 109134454

(51) Int. Cl.
*A61K 31/04* (2006.01)
*A61K 31/4412* (2006.01)
*A61P 31/04* (2006.01)
*A61K 35/74* (2015.01)

(52) U.S. Cl.
CPC .......... *A61K 31/4412* (2013.01); *A61K 35/74* (2013.01); *A61P 31/04* (2018.01)

(58) Field of Classification Search
CPC ...... A61K 31/4412; A61K 35/74; A61P 31/04
See application file for complete search history.

(56) References Cited

U.S. PATENT DOCUMENTS

| | | | |
|---|---|---|---|
| 2010/0093538 A1 | 4/2010 | Gnanamanickam | |
| 2018/0064769 A1* | 3/2018 | McKenna | A61K 35/747 |
| 2022/0010448 A1 | 1/2022 | Zhang et al. | |
| 2022/0010450 A1 | 1/2022 | Takahashi et al. | |
| 2022/0104500 A1* | 4/2022 | Yang | A01N 63/27 |

FOREIGN PATENT DOCUMENTS

| | | |
|---|---|---|
| WO | 20130130680 A1 | 9/2013 |
| WO | 202000187822 A1 | 9/2020 |
| WO | 20200246609 A1 | 12/2020 |

OTHER PUBLICATIONS

Gauthier et al. 2019 (Stimulated Growth and Innate Immunity in Brook Charr (*Salvelinus fontinalis*) Treated with a General Probiotic (Bactocell TM) and Two Endogenous Probiotics that Inhibit Aeromonas salmonicida in vitro; Microorganisms 7(193): 1-17). (Year: 2019).*
Woo and Bahna Clinical and Translational Allergy 2011, 1:3.
International Searching Authority Search Report for PCT/US20/54303, dated Jun. 29, 2021.
International Searching Authority Written Opinion for PCT/US20/54303, dated Jun. 29, 2021.
International Searching Authority Search Report for PCT/US21/53405, dated Jul. 2, 2022.
International Searching Authority Written Opinion for PCT/US21/53405, dated Jul. 2, 2022.
International Searching Authority ISR and WO Transmittal for PCT/US21/53405, dated Jul. 2, 2022.
Swan, George A., "Isolation, Structure, and Synthesis of Hermidin, A Chromogen From *Mercurialis perennis* L." J. Chem. Soc., Perkin Trans. 1, 1985, 1757-1766.
International Searching Authority Search Report for PCT/US21/53482, dated Nov. 2, 2022.
International Searching Authority Written Opinion for PCT/US21/53482, dated Nov. 2, 2022.
International Searching Authority ISR and WO Transmittal for PCT/US21/53482, dated Jul. 2, 2022.
Office Action issued for USPA U.S. Appl. No. 17/063,540, dated Oct. 6, 2022.
Gram, Lone, Jette Melchiorsen, Bettina Spanggaard, Ingrid Huber, and Torben F. Nielsen. "Inhibition of Vibrio anguillarum byPseudomonas fluorescens AH2, a Possible Probiotic Treatment of Fish." Applied and Environmental Microbiology 65.3 (1999)969.

(Continued)

*Primary Examiner* — Mary Maille Lyons
(74) *Attorney, Agent, or Firm* — Klintworth & Rozenblat IP LLP

(57) ABSTRACT

The present disclosure concerns methods of using novel bacterial strains of 0617-T307, 0917-T305, 0917-T306, 0917-T307, 0118-T319, 0318-T327, and 0418-T328, the cell broth and novel metabolites produced from the bacterial strains, that can inhibit the growth of a variety of fish pathogens. The methods include use of novel, potent antimicrobial metabolites produced from the strains corresponding to a compound having Formula (I):

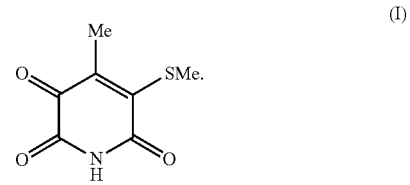

(I)

21 Claims, No Drawings

(56) References Cited

OTHER PUBLICATIONS

Eissa, Nour; Abou ElGheit, Elsayed; Shaheen, Adel. (2014). Protective Effect of Pseudomonas Fluorescens as a Probiotic in Controlling Fish Pathogens. American Journal of BioScience. 2. 175-181.
Wu, L. et al. "Identification of Pseudomonas mosselii BS011 gene clusters required for suppression of Rice Blast Fungus *Magnaporthe oryzae*" J. Biotechnology, vol. 282, 1-9.
Smith, P. et al. "Evidence for the competitive exclusion of aeromonas salmonicida from fish with stress-inducible furunculosis by a fluorescent pseudomonad" J. Fish Disease, 16(5), 521-524.
Adaskaveg JE, Förster H & Wade ML (2010) Effectiveness of Kasugamycin against Erwinia amylovora and its potential use for managing fire blight of pear. Plant Disease 95: 448-454.
Aldwinckle H.S., Bhaskara Reddy M.V., Norelli J.L. (2002) Evaluation of control of fire blight infection of apple blossoms and shoots with sar inducers, biological agents, a growth regulator, copper compounds, and other materials, International Society for Horticultural Science (ISHS), Leuven, Belgium, pp. 325-331.
Alsohim A.S., Taylor T.B., Barrett G.A., Gallie J., Zhang X.X., Altamirano-Junqueira A.E., Johnson L.J., Rainey P.B., Jackson R.W. (2014) The biosurfactant viscosin produced by Pseudomonas fluorescens SBW25 aids spreading motility and plant growth promotion. Environ Microbiol 16:2267-81.
Biondi E., Bazzi C., Vanneste J.L. (2006) Reduction of fire blight incidence on apple flowers and colonisation of pear shoots in experimental orchards using *Pseudomonas* spp. IPV-BO G19 and IPV-BO 3371, International Society for Horticultural Science (ISHS), Leuven, Belgium, pp. 323-328.
Bourhis, L.J., Dolomanov, O.V., Gildea, R.J., Howard, J.A.K., Puschmann, H. (2015). The anatomy of a comprehensive constrained, restrained refinement program for the modern computing environment—Olex2 dissected Acta Cryst A71:59-75.
Broggini G.A.L., Duffy B., Holliger E., Schärer H.J., Gessler C., Patocchi A. (2005) Detection of the fire blight biocontrol agent Bacillus subtilis BD170 (Biopro®) in a Swiss apple orchard. Eur J Plant Pathol 111:93-100.
Cabrefiga J., Frances J., Montesinos E., Bonaterra A. (2011) Improvement of fitness and efficacy of a fire blight biocontrol agent via nutritional enhancement combined with osmoadaptation. Appl Environ Microbiol 77:3174-81.
Chen X.H., Scholz R., Borriss M., Junge H., Mogel G., Kunz S., Borriss R. (2009) Difficidin and bacilysin produced by plant-associated Bacillus amyloliquefaciens are efficient in controlling fire blight disease. J Biotechnol 140:38-44.
Dabboussi, F., Hamze, M., Singer, E., Geoffroy, V., Meyer, J., & Izard, D. (2002). *Pseudomonas mosselii* sp . nov ., a novel species isolated from clinical specimens. Int J Syst Bacteriol, 52: 363-376.
Dolomanov, O.V., Bourhis, L.J., Gildea, R.J, Howard, J.A.K. & Puschmann, H. (2009), OLEX2: a complete structure solution, refinement and analysis program. J Appl Cryst 42:339-341.
Galasso O., Sponza G., Bazzi C., Vanneste J.L. (2002) Characterisation of two fluorescent strains of Pseudomonas as biocontrol agents against fire blight, International Society for Horticultural Science (ISHS), Leuven, Belgium, pp. 299-307.
García-Valdés E., Lalucat J. (2016) Pseudomonas: Molecular phylogeny and current taxonomy, in: R. S. Kahlon (Ed.), Pseudomonas: Molecular and Applied Biology, Springer.
Gavrish, E., Bollmann, A., Epstein, S., & Lewis, K. (2008). A trap for in situ cultivation of filamentous actinobacteria. J Microbiol Methods 72:257-262.
Guindon S., Gascuel O. (2003) A simple, fast, and accurate algorithm to estimate large phylogenies by maximum likelihood. Syst Biol 52:696-704.
Gwinn K.D. (2018) Chapter 7—Bioactive natural products in plant disease control, in: R. Atta ur (Ed.), Studies in Natural Products Chemistry, Elsevier. pp. 229-246.

Haas D., Défago G. (2005) Biological control of soil-borne pathogens by fluorescent pseudomonads. Nat Rev Microbiol 3:307.
Hamamoto, H., Urai, M., Ishii, K., Yasukawa, J., Paudel, A., Murai, M., Kaji, T., Kuranaga, T., Hamase, K., Katsu, T., Su, J., Adachi, T., Uchida, R., Tomoda, H., Yamada, M., Souma, M., Kurihara, H., Inoue, M., & Sekimizu, K. (2015). Lysocin e is a new antibiotic that targets menaquinone in the bacterial membrane. Nat Chem Biol 11:127-133.
Johnson K.B. S.V.O. (2000) Biological control of fire blight, in: e. J.L. Vanneste (Ed.), Fire Blight: the Disease and its Causative Agent, Erwinia amylovora, CABI Publishing, Wallingford, UK. . pp. 319-338.
Knackmuss, H., Medizinische, M., & Chemie, I. (1968). Methyl-substituted 2,3,6-trihydroxypyridines and their oxidation products. Eur. J. Inorg. Chem. 2689: 2679-2689.
Kunz S., Schmitt A., Haug P. (2011) Development of strategies for fire blight control in organic fruit growing, International Society for Horticultural Science (ISHS), Leuven, Belgium pp. 431-436.
Laux P., Wesche, J., Zeller, W. (2003) Field experiments on biological control of fire blight by bacterial antagonists. J. Plant Disease Prot. 110:401-407.
Li W., Rokni-Zadeh H., De Vleeschouwer M., Ghequire M.G., Sinnaeve D., Xie G.L., Rozenski J., Madder A., Martins J.C., De Mot R. (2013) The antimicrobial compound xantholysin defines a new group of Pseudomonas cyclic lipopeptides. PLoS One 8:e62946.
Lindow S.E., McGourty G., Elkins R. (1996) Interactions of antibiotics with Pseudomonas fluorescens strain A506 in the control of fire blight and frost injury to pear. Phytopathology 86:841-848.
Loots, D. T., Erasmus, E., & Mienie, L. J. (2005). Identification of 19 new metabolites induced by abnormal amino acid conjugation in isovaleric acidemia. Clin Chem, 51: 1510-1512.
Masschelein J., Jenner M., Challis G.L. (2017) Antibiotics from Gram-negative bacteria: a comprehensive overview and selected biosynthetic highlights. Nat Prod Rep 34:712-783.
Mikiciński A., Puławska J., Molzhigitova A., Sobiczewski P. (2020) Bacterial species recognized for the first time for its biocontrol activity against fire blight (*Erwinia amylovora*). Eur J Plant Pathol. 156:257-272.
Mikiciński A.S., P.; Berczyński. S. (2008) Selection of bacteria from epiphytic populations on apple trees and soil environment for ability to control fire blight (*Erwinia amylovora*). Phytopathol. Pol. 47:43-55.
Norelli J.L., Jones A.L., Aldwinckle H.S. (2003) Fire blight management in the twenty-first century—Using new technologies that enhance host resistance in apple. Plant Disease 87:756-765.
Osipov, A. M., Metlova, L. P., Baranova, N. V, & Rudakov, E. S. (1978). New derivatives of difuryl: 2,2'-difuryl-5,5'-dicarbinol and 2,2'-difuryl-5,5'-dicarboxylic acid. Ukrainskii Khimicheskii Zhurnal (Russian Edition), 44: 398.
Pascual, J., García-López, M., Carmona, C., Sousa, T. da S., de Pedro, N., Cautain, B., Martín, J., Vicente, F., Reyes, F., Bills, G. F., & Genilloud, O. (2014). *Pseudomonas soli* sp. nov., a novel producer of xantholysin congeners. Syst Appl Microbiol, 37: 412-416.
Paulin J.P. (1978) Biological control of fire blight: Preliminary experiments, Proceedings of the 2 International Conference Plant Pathogenic Bacteria, pp. 525.
Peix A., Ramírez-Bahena M.-H., Velázquez E. (2018) The current status on the taxonomy of Pseudomonas revisited: An update. Infect Genet Evol. 57:106-116.
Pujol M, Badosa E, Manceau C & Montesinos E (2006) Assessment of the environmental fate of the biological control agent of fire blight, Pseudomonas fluorescens EPS62e, on apple by culture and real-time PCR methods. Appl Environ Microb 72: 2421-2427.
Sheldrick, G.M. (2008). A short history of SHELX. Acta Cryst. A64:112-122.
Sheldrick, G.M. (2015). Crystal structure refinement with SHELXL Acta Cryst. C71:3-8.
Stockwell V.O.D. B. (2012) Use of antibiotics in plant agriculture. Rev. Sci. Tech. Off. Int Epiz. 31:199-210.

(56) References Cited

OTHER PUBLICATIONS

Thomson S.V. S.M.N., Moller W.J., Reil W.O. (1976) Efficacy of bactericides and saprophytic bacteria in reducing colonization and infection of pear flowers by *Erwinia amylovora*. Phytopathology 66:1457-1459.

DuPont, Tianna, Johnson; Rachel, Elkins; Tim, Smith; David, Granatstein. (2018) Organic Fire Blight Management in the Western U.S.—extension, Organic agriculture.

Vrancken K., Holtappels M., Schoofs H., Deckers T., Valcke R. (2013) Pathogenicity and infection strategies of the fire blight pathogen *Erwinia amylovora* in Rosaceae: state of the art. Microbiology 159:823-32.

Wilson M., Epton H.A.S., Sigee D.C. (1992) Biological-control of fire blight of Hawthorn (Crataegus-Monogyna) with fluorescent *Pseudomonas* spp under protected conditions. Journal of Phytopathology—Phytopathologische Zeitschrift 136:16-26.

International Search Report for International Patent Application No. PCT/US21/53482, dated Feb. 11, 2022.

Written Opinion for International Patent Application No. PCT/US21/53482, dated Feb. 11, 2022.

Banu, L., Conrads, G., Rehrauer, H., Hussain, H., Allan, E., & van der Ploeg, J. R. (2010). The *Streptococcus mutans* serine/threonine kinase, PknB, regulates competence development, bacteriocin production, and cell wall metabolism. Infect Immun, 78: 2209-2220.

Eszterbauer, E., Hardy, T., Rónai, Z, Sipos, D., Zsigmond, G. (2020) Cryopreservation of three *Saprolegnia species* (*Oomycota*): Preliminary evidence for the long-term archiving of water mould species, Fungal Biology, 124: 682-687.

Ishiguro, E., Kay, W., Ainsworth, T., Chamberlain, J., Austen, R., Buckley, J., Trust, T. (1981) Loss of virulence during culture of Aeromonas salmonicida at high temperature. J Bacteriol. 148(1):333-40.

Mabrok, M., Machado, M., Serra, C.R., Afonso, A., Valente, L.M.P. and Costas, B. (2016), Tenacibaculosis induction in the Senegalese sole (Solea senegalensis) and studies of Tenacibaculum maritimum survival against host mucus and plasma. J Fish Dis, 39: 1445-1455.

Onarinde, B., & Dixon, R. (2018). Prospects for Biocontrol of Vibrio parahaemolyticus Contamination in Blue Mussels (*Mytilus edulus*)—A Year-Long Study. Frontiers in microbiology, 9, 1043.

Soliman WS, Shaapan RM, Mohamed LA, Gayed SSR. (2019) Recent biocontrol measures for fish bacterial diseases, in particular to probiotics, bio-encapsulated vaccines, and phage therapy. Open Vet J. 9(3): 190-195.

\* cited by examiner

PSEUDOMONAS STRAINS AND THEIR METABOLITES TO CONTROL FISH DISEASES

CROSS-REFERENCE TO RELATED APPLICATIONS

This application is a continuation-in-part application of U.S. patent application Ser. No. 17/063,540, filed Oct. 5, 2020 and U.S. patent application Ser. No. 17/493,594, filed Oct. 4, 2021, both entitled "PSEUDOMONAS STRAINS AND THEIR METABOLITES TO CONTROL PLANT DISEASES," and claims priority to same, as well as to International Patent Application No. PCT/US2020/54303, filed Oct. 5, 2020, International Patent Application No. PCT/US2021/53405, filed Oct. 4, 2021, Argentina Patent Application Serial No. P 20 01 02757, filed Oct. 5, 2020, and Taiwan Patent Application Serial No. 109134454, filed Oct. 5, 2020, the contents of each application which are herein incorporated by reference in their entirety.

FIELD OF THE INVENTION

This invention is in the field of biopesticides. In particular, the invention pertains to seven novel strains of *Pseudomonas* spp, 0617-T307, 0917-T305, 0917-T306, 0917-T307, 0118-T319, 0318-T327, and 0418-T328, the cell broth and novel metabolites produced from the bacterial strain that can inhibit the growth of a variety of fish pathogens. The *Pseudomonas* strains of 0617-T307, 0917-T305, 0917-T306, 0917-T307, 0118-T319, 0318-T327, and 0418-T328 have been deposited in the American Type Culture Collection (ATCC) and have ATCC accession number PTA-126796, PTA-126797, PTA-126798, PTA-126799, PTA-126800, PTA-126801, and PTA-126802, respectively.

BACKGROUND OF THE INVENTION

Wild fish, farmed fish, and ornamental pet fish are susceptible to infectious diseases caused by a variety of bacterial pathogens. The most frequently described fish bacterial pathogens are *Aeromonas, Edwardsiella, Pseudomonas, Shewanella, Mycobacterium, Streptococcus, Flavobacterium*, and *Vibrio*. *Aeromonas salmonicida* causes furunculosis, haemorrhages, muscle lesions, inflammation of the lower intestine, spleen enlargement, and death in freshwater fish populations. Vibriosis caused by *Vibrio* species is responsible for mass mortality in marine ornamental fishes. Common symptoms of *Vibrio* infected fishes include dark skin, pale gills, haemorrhages at the base of fins, exophthalmia, skin ulcers, corneal opacity, splenomegaly, and enteritis. *V. parahaemolyticus* is found to be the causative agent of tail rot disease in marine ornamental fish. The bacterium attacks the adipose fin, and progressive infection is always fatal. Two Gram-positive bacterial species, *Streptococcus agalactiae* and *Streptococcus iniae*, also cause severe impact to the aquaculture industry. *S. agalactiae* causes meningitis in fish, and infected survival often shows neurological disorders, such as constant, aberrant swimming. *S. agalactiae* has become a major pathogen for tilapia. Freshwater and saltwater fish are susceptible to infection by *S. iniae*. *S. iniae* causes meningoencephalitis, skin lesions, and septicemia. *S. iniae* infections have been reported in at least 27 species of cultured or wild fish and, resulting in over US$100M in annual losses. *S. iniae* can cause disease in mammals, including humans. Fish handlers with hand injuries can become ill from a Strep infection after contacting *S. iniae* infected fish. *Tenacibaculum maritimum* is a bacterial pathogen that affects a large number of marine fish species in the world and is of considerable economic significance to aquaculture producers. The pathogen causes tenacibaculosis (an ulcerative disease), which is one of the most threatening of many species of commercial value. Apart from bacterial pathogens, oomycete pathogen *Saprolegnia parasitica* is both a saprotroph and necrotroph. The pathogen causes saprolegniasis, a disease that is characterized by visible white or grey patches of filamentous mycelium on the body or fins of freshwater fish. *Saprolegnia* infections were kept under control with malachite green. However, banning the use of malachite green resulted in a dramatic re-emergence of *Saprolegnia* infections in aquaculture. *S. parasitica* is now causing economic impacts, especially on catfish, salmon, and trout species.

There is a need for new biopesticides derived from novel strains, cell broths and novel metabolites produced from such strains that can inhibit the growth of fish disease-causing pathogens.

BRIEF SUMMARY OF THE INVENTION

In a first aspect, a method of controlling a fish pathogen and associated disease of a fish is provided. The method includes several steps. One step includes producing an agricultural composition comprising Formula (I)

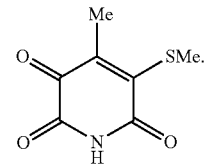 [SMILES: CSC1=C(C)C(=O)C(=O)NC1=O]

(Formula (I))

Another step includes applying said agricultural composition to the fish to inhibit the growth of the fish pathogen and the associated disease on the fish.

In a second aspect, a method of controlling a fish pathogen disease is provided. The method includes a step of applying an agricultural composition comprising between about $1.0 \times 10^5$ and $1.0 \times 10^9$ cfu per mL *Pseudomonas* bacteria to fish to inhibit the growth of a fish pathogen and an associated disease.

DETAILED DESCRIPTION

The present invention relates to a novel metabolite produced by seven *Pseudomonas* strains listed in this patent, such as 0617-T307, that exhibits antimicrobial activity against pathogenic microorganisms, including bacteria and fungi. From the 16S rRNA and other housekeeping gene sequences, the strain was identified as *Pseudomonas soli* 0617-T307 in the *Pseudomonas putida* group. The cell broth of the 7 bacterial strains, such as 0617-T307, contains a novel, potent 6-membered heterocycle natural product which is designated as RejuAgro A (Formula (I)) as depicted below:

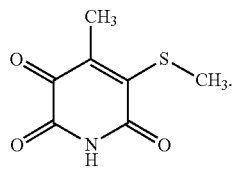

(I)

This compound, its method of production, and applications for inhibiting fish microbial pathogens is disclosed in greater detail herein.

Definitions

When introducing elements of aspects of the disclosure or particular embodiments, the articles "a," "an," "the," and "said" are intended to mean that there are one or more of the elements. The terms "comprising," "including," and "having" are intended to be inclusive and mean that there may be additional elements other than the listed elements. The term "or" means any one member of a particular list and also includes any combination of members of that list, unless otherwise specified.

As intended herein, the terms "substantially," "approximately," and "about" and similar terms are intended to have a broad meaning in harmony with the common and accepted usage in the art to which the subject matter of this disclosure pertains. It should be understood by those of skill in the art who review this disclosure that these terms are intended to allow a description of certain features described and claimed without restricting the scope of these features to precise numerical ranges provided. Accordingly, these terms should be interpreted as indicating that insubstantial or inconsequential modifications or alterations of the subject matter described and claimed are considered to be within the scope of the invention as recited in the appended claims.

"Biological control agents (or BCAs)" are a way of managing pests, such as pathogens, weeds and insects, safely, sustainably, and cost-effectively. These agents are introduced into the environment to target a pest species, with the aim of reducing the pest's population or abundance in the environment.

"Biologicals" are preparations of living microorganisms (bacteria and yeasts) that produce colonies on the hosts. These microorganisms are applied mainly to slow the pathogen buildup during its infection (Soliman et al. (2019) and Tianna et al. (2018)).

"Biorational" is a term applied to microbe-based biopesticides. These biopesticides are often made by fermenting microbial strains. Most of these products have both anti-bacterial and anti-fungal activity (Soliman et al. (2019) and Tianna et al. (2018)).

"Biopesticides" is defined by The US Environmental Protection Agency (EPA) to be pesticides derived from natural materials and categorizes them as either biochemical pesticides, containing substances that control pests by non-toxic mechanisms, microbial pesticides, consisting of microorganisms that typically produce bioactive natural products (BNPs), or plant-incorporated-protectants with activity produced by plants because of added genetic materials (Gwinn K. D. (2018)).

The compound referred to as RejuAgro A corresponds to chemical compound having the formula (I), respectively, as illustrated below:

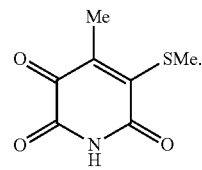 [SMILES: CSC1=C(C)C(=O)C(=O)NC1=O]

(I)

In a first aspect, a method of controlling a fish pathogen and associated disease of a fish is provided. The method includes several steps. One step includes producing an agricultural composition comprising Formula (I)

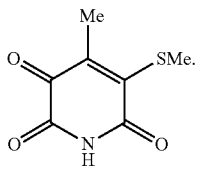

(Formula (I))

Another step includes applying said agricultural composition to the fish to inhibit the growth of the fish pathogen and the associated disease on the fish.

In a first respect, the method includes the fish pathogen being selected from the group consisting of *Aeromonas salmonicida, Streptococcus agalactiae, Streptococcus iniae, Vibrio parahaemolyticus, Saprolegnia parasitica*, and *Tenacibaculum maritimum*. In a second respect, the method includes the associated disease being selected from the group consisting of furunculosis, streptococcosis, vibriosis, acute hepatopancreatic necrosis disease, saprolegniasis, and tenacibaculosis. In a third respect, the method includes the fish being selected from the group consisting of Salmon, Trout, Cyprinids, Pike, Perch, Bullheads, Turbot, Halibut, fresh-water fish, sea-water fish, wild fish, farm fish, fish, shrimp, squid, oyster, crab, and conch.

In a second aspect, a method of controlling a fish pathogen disease is provided. The method includes a step of applying an agricultural composition comprising between about $1.0\times10^5$ and $1.0\times10^9$ cfu per mL *Pseudomonas* bacteria to fish to inhibit the growth of a fish pathogen and an associated disease.

In a first respect, the method includes the *Pseudomonas* bacteria being selected from the group consisting of *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802). In a second respect, the method includes the composition comprising between about $5.0\times10^7$ and $2.0\times10^8$ cfu per mL *Pseudomonas* bacteria. In a third respect, the method includes the fish pathogen being selected from the group consisting of *Aeromonas salmonicida, Streptococcus agalactiae, Streptococcus iniae, Vibrio parahaemolyticus, Saprolegnia parasitica*, and *Tenacibaculum maritimum*. In a fourth respect, the method includes the associated disease being selected from the group consisting of furunculosis, streptococcosis, vibriosis, acute hepatopancreatic necrosis disease, saprolegniasis, and tenacibaculosis. In a fifth respect, the method includes the fish being selected from the group consisting of Salmon, Trout, Cyprinids, Pike, Perch, Bullheads, Turbot, Halibut, fresh-water fish, sea-water fish, wild fish, farm fish, fish, shrimp, squid, oyster, crab, and conch.

Biological Deposit Information

One of the inventors, Dr. Ching-Hong Yang, submitted the bacterial strains *Pseudomonas soli* 0617-T307, *Pseudomonas soli* 0917-T305, *Pseudomonas soli* 0917-T306, *Pseudomonas soli* 0917-T307, *Pseudomonas mosselii* 0118-T319, *Pseudomonas mosselii* 0318-T327, and *Pseudomonas mosselii* 0418-T328 to the American Type Culture Collection (ATCC®), P.O. Box 1549, Manassas, Va. 20110 USA ("ATCC Patent Depository") on Jun. 25, 2020, which were accorded unofficial ATCC patent numbers PTA-126796, PTA-126797, PTA-126798, PTA-126799, PTA-126800, PTA-126801, and PTA-126802, respectively. Following viability testing, the ATCC Patent Depository accorded these deposited bacterial strains the following Accession numbers, effective Jun. 25, 2020: *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802). Dr. Yang grants permission to Applicant to include this biological deposit disclosure in the present application.

EXAMPLES

Example 1

Use of RejuAgro A for Inhibiting Fish Pathogens

Fish pathogens were grown in their respective broth and temperature (Table 1) to exponential phase. After incubation, broth cultures were diluted 1:10 and pipetted into individual well of 96 well plates containing the compound per concentration (0.39, 0.78, 1.56, 3.13, 6.25, 12.5, 25, 50, 100, 200m/m1). In addition, pathogen control and blank control (media only) were included. The optical density (OD600) readings from each well were captured using a spectrophotometer to determine MIC. The pathogen control and technical replicates of each concentration were combined, and 100 µl plated on respective agar in triplicate to determine the final MIC. The MICs of RejuAgro A on *Aeromonas salmonicida*, *Streptococcus agalactiae*, *Streptococcus iniae*, *Vibrio parahaemolyticus*, and *Tenacibaculum maritimum* are 1.56, 1.56, 3.13, 0.39, and 12.5 µg/ml, respectively. The minimum lethal concentration (MLC) was determined in triplicate. The MLC of RejuAgro A on *Saprolegnia parasitica* is 100 µg/ml. These results demonstrate that RejuAgro A provides good inhibition on furunculosis, streptococcosis, saprolegniasis, and tenacibaculosis caused by *Aeromonas salmonicida, Streptococcus agalactiae, Streptococcus* iniae, *Saprolegnia parasitica*, and *Tenacibaculum maritimum*. RejuAgro A also shows inhibition on vibriosis, acute hepatopancreatic necrosis disease, and contamination in fish, shrimp, squid, oyster, crab, and conch caused by *Vibrio parahaemolyticus*.

TABLE 1

Summary of the antimicrobial effect of RejuAgro A on different fish pathogens

| Strain (related disease) | Medium/Temperature | MIC (µg/mL) RejuAgro A | MLC (µg/mL) RejuAgro A |
|---|---|---|---|
| *Aeromonas salmonicida* (furunculosis in Salmon, Trout, Cyprinids, Pike, Perch, Bullheads, Turbot, and Halibu) | (TSA/TSB)/20° C. | 1.56 | — |
| *Streptococcus agalactiae* (streptococcosis in fresh and sea-water fish) | (TSAY/TSBY)/28° C. | 1.56 | — |
| *Streptococcus iniae* (streptococcosis in fresh and sea-water fish) | (TSAY/TSBY)/28° C. | 3.13 | — |
| *Vibrio parahaemolyticus* (vibriosis, acute hepatopancreatic necrosis disease and contamination in fish, shrimp, squid oyster, crab, and conch) | (TSA2/TSB2)/37° C. | 0.39 | — |
| *Tenacibaculum maritimum* (tenacibaculosis in marine fish) | (MA/MB)/15° C. | 12.5 | — |
| *Saprolegnia parasitica* (saprolegniasis in wild and farm fish) | GY/20° C. | NA | 100 |

NA: Not applicable for isolate
"—" Not available

Example 2

Media Culture Compositions Used in the Examples

Table 2 includes exemplary media compositions used in the Examples.

TABLE 2

Media compositions.

| No. | Medium Name | Composition | g per liter | Reference |
|---|---|---|---|---|
| M1 | YME | Yeast extract | 4.0 g | (Hamamoto, H., et. al. (2015)) |
|  |  | Malt extract | 10 g |  |
|  |  | Glucose | 4.0 g |  |
|  |  | Tap water | 1.0 L |  |
| M6 | DAPG medium | Malt extract | 15.0 g | (Gnanamanickam, Samuel S. (2008)) |
|  |  | Water |  |  |
| M7 | PRN medium | Glycerol | 30.0 g | (Gnanamanickam, Samuel S. (2008)) |
|  |  | $K_2HPO_4$ | 3.0 g |  |
|  |  | NaCl | 5.0 g |  |
|  |  | $MgSO_4 \cdot 7H_2O$ | 0.5 g |  |
|  |  | D-tryptophan | 0.61 g |  |
| M8 | IAA medium | D-glucose | 5.0 g | (Gnanamanickam, Samuel S. (2008)) |
|  |  | Casamino acids | 25.0 g |  |
|  |  | $MgSO_4 \cdot 7H_2O$ | 0.3 g |  |
|  |  | $K_2HPO_4$ | 1.7 g |  |
|  |  | $NaH_2PO_4$ | 2.0 g |  |
| M9 | CN | Casamino acids | 10.0 g | (Gavrish, E., et al. (2008)) |
|  |  | Nutrient broth | 10.0 g |  |
| M10 | TSA/TSB | Tryptic soy broth | 30.0 g | (Ishiguro, E., et al. (1981)) |
|  |  | Agar (TSA only) | 15.0 g |  |
| M11 | TSAY/TSBY | Tryptic soy broth | 30.0 g | (Banu, L, et al. (2010)) |
|  |  | Yeast extract | 5.0 g |  |
|  |  | Agar (TSAY only) | 15.0 g |  |
| M12 | TSA2/TSB2 | Tryptic soy broth | 30.0 g | (Onarinde, B., & Dixon, R. (2018)) |
|  |  | NaCl | 15.0 g |  |
|  |  | Agar (TSA2 only) | 15.0 g |  |
| M13 | MA/MB | Marine broth | 37.4 g | (Mabrok M., et al. (2016)) |
|  |  | Agar (MA only) | 15.0 g |  |
| M14 | GY | Glucose | 10.9 g | (Eszterbauer, et al. (2020) |
|  |  | Yeast extract | 2.5 g |  |
|  |  | Agar | 15.0 g |  |

Example 3

Bacterial Strains, Natural Products, and References Cited to Same

The bacterial strains and natural products described in this application and presented in the appended claims are well-known in the microbiology literature. These references are presented below in Table 3 for each of the cited bacterial strains and natural products disclosed herein, the contents of which are hereby incorporated by reference in their entirety.

TABLE 3

Bacterial strains, natural products and references cited in support as evidence of their availability.

| | Reference citation |
|---|---|
| Bacterial Strains | |
| 0617-T307, 0917-T305, 0917-T306, and 0917-T307 | Pascual, J., García-López, M., Carmona, C., Sousa, T. da S., de Pedro, N., Cautain, B., Martin, J., Vicente, F., Reyes, F., Bills, G. F., & Genilloud, O. (2014). *Pseudomonas soli* sp. nov., a novel producer of xantholysin congeners. *Syst Appl Microbiol*, 37: 412-416. |
| 0118-T319, 0318-T327, and 0418-T328 | Dabboussi, F., Hamze, M., Singer, E., Geoffroy, V., Meyer, J., & Izard, D. (2002). *Pseudomonas mosselii* sp. nov., a novel species. *Int J Syst Bacteriol*, 52: 363-376. |
| Natural Products | |
| RejuAgro B | Knackmuss, H., Medizinische, M., & Chemie, I. (1968). Methyl-substituted 2,3,6-trihydroxypyridines and their oxidation products. *Eur. J. Inorg. Chem.* 2689: 2679-2689. |
| Rt22.9 and Rt25.0 | Loots, D. T., Erasmus, E., & Mienie, L. J. (2005). Identification of 19 new metabolites induced by abnormal amino acid conjugation in isovaleric acidemia. *Clin Chem*, 51: 1510-1512. |
| Rt18.9 | Osipov, A. M., Metlova, L. P., Baranova, N. V, & Rudakov, E. S. (1978). New derivatives of difuryl: 2,2'-difuryl-5,5'-dicarbinol and 2,2'-difuryl-5,5'-dicarboxylic acid. *Ukrainskii Khimicheskii Zhurnal* (Russian Edition), 44: 398. |

CITATIONS

Banu, L., Conrads, G., Rehrauer, H., Hussain, H., Allan, E., & van der Ploeg, J. R. (2010). The *Streptococcus mutans* serine/threonine kinase, PknB, regulates competence development, bacteriocin production, and cell wall metabolism. *Infect Immun,* 78: 2209-2220.

Dabboussi, F., Hamze, M., Singer, E., Geoffroy, V., Meyer, J., & Izard, D. (2002). *Pseudomonas mosselii* sp. nov., a novel species. *Int Syst Bacteriol,* 52: 363-376.

Eszterbauer, E., Hardy, T., Rònai, Z, Sipos, D., Zsigmond, G. (2020) Cryopreservation of three *Saprolegnia* species (*Oomycota*): Preliminary evidence for the long-term archiving of water mould species, *Fungal Biology,* 124: 682-687.

Gavrish, E., Bollmann, A., Epstein, S., & Lewis, K. (2008). A trap for in situ cultivation of filamentous actinobacteria. *J Microbiol Methods* 72:257-262.

Gnanamanickam, Samuel S. (Roanoke, V A, U. (2010). *Pseudomonas bacterium* (Patent No. 20100093538)

Gwinn K. D. (2018) Chapter 7—Bioactive natural products in plant disease control, in: R. Atta ur (Ed.), Studies in Natural Products Chemistry, Elsevier. pp. 229-246.

Hamamoto, H., Urai, M., Ishii, K., Yasukawa, J., Paudel, A., Murai, M., Kaji, T., Kuranaga, T., Hamase, K., Katsu, T., Su, J., Adachi, T., Uchida, R., Tomoda, H., Yamada, M., Souma, M., Kurihara, H., Inoue, M., & Sekimizu, K. (2015). Lysocin e is a new antibiotic that targets menaquinone in the bacterial membrane. *Nat Chem Biol* 11:127-133.

Ishiguro, E., Kay, W., Ainsworth, T., Chamberlain, J., Austen, R., Buckley, J., Trust, T. (1981) Loss of virulence during culture of *Aeromonas salmonicida* at high temperature. *J Bacteriol.* 148(1):333-40.

Knackmuss, H., Medizinische, M., & Chemie, I. (1968). Methyl-substituted 2,3,6-trihydroxypyridines and their oxidation products. *Eur. J. Inorg. Chem.* 2689: 2679-2689.

Loots, D. T., Erasmus, E., & Mienie, L. J. (2005). Identification of 19 new metabolites induced by abnormal amino acid conjugation in isovaleric acidemia. *Clin Chem,* 51: 1510-1512.

Mabrok, M., Machado, M., Serra, C. R., Afonso, A., Valente, L. M. P. and Costas, B. (2016), Tenacibaculosis induction in the Senegalese sole (*Solea senegalensis*) and studies of *Tenacibaculum maritimum* survival against host mucus and plasma. *J Fish Dis,* 39: 1445-1455.

Onarinde, B., & Dixon, R. (2018). Prospects for Biocontrol of *Vibrio parahaemolyticus* Contamination in Blue Mussels (*Mytilus edulus*)—A Year-Long Study. *Frontiers in microbiology,* 9, 1043.

Osipov, A. M., Metlova, L. P., Baranova, N. V, & Rudakov, E. S. (1978). New derivatives of difuryl: 2,2'-difuryl-5,5'-dicarbinol and 2,2'-difuryl-5,5'-dicarboxylic acid. *Ukrainskii Khimicheskii Zhurnal* (Russian Edition), 44: 398.

Pascual, J., García-López, M., Carmona, C., Sousa, T. da S., de Pedro, N., Cautain, B., Martin, J., Vicente, F., Reyes, F., Bills, G. F., & Genilloud, O. (2014). *Pseudomonas soli* sp. nov., a novel producer of xantholysin congeners. *Syst Appl Microbiol,* 37: 412-416.

Soliman W S, Shaapan R M, Mohamed L A, Gayed S S R. (2019) Recent biocontrol measures for fish bacterial diseases, in particular to probiotics, bio-encapsulated vaccines, and phage therapy. Open Vet J. 9(3): 190-195.

Tianna D. K., Johnson; Rachel, Elkins; Tim, Smith; David, Granatstein. (2018) Organic Fire Blight Management in the Western U.S.—eXtension, Organic agriculture.

INCORPORATION BY REFERENCE

All literature, publications, patents, patent applications, and related material cited here are incorporated by reference as if fully set forth herein.

What is claimed is:

1. A method of controlling a fish pathogen and associated disease of a fish, comprising the steps of
   (i) producing a composition from *Pseudomonas soli* or *Pseudomonas mosselii* comprising a bacterial metabolite of Formula (I)

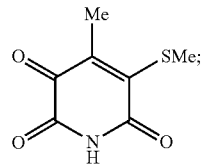

and
   (ii) applying said composition to the fish to inhibit the growth of the fish pathogen and the associated disease on the fish.

2. The method of claim 1, wherein the fish pathogen is selected from the group consisting of *Aeromonas salmonicida*, *Streptococcus agalactiae*, *Streptococcus iniae*, *Vibrio parahaemolyticus*, *Saprolegnia parasitica*, and *Tenacibaculum maritimum*.

3. The method according to claim 1, wherein the associated disease is selected from the group consisting of fish columnaris disease, furunculosis, streptococcosis, vibriosis, acute hepatopancreatic necrosis disease, saprolegniasis, and tenacibaculosis.

4. The method according to claim 1, wherein the fish is selected from the group consisting of fresh-water fish and sea-water fish.

5. A method of controlling a fish pathogen disease, comprising:
   applying a composition comprising between about $1.0 \times 10^5$ and $1.0 \times 10^9$ cfu per mL *Pseudomonas* bacteria to fish to inhibit the growth of a fish pathogen and an associated disease,
   wherein the *Pseudomonas* bacteria is selected from the group consisting of *Pseudomonas soli* and *Pseudomonas mosselii*.

6. The method of claim 5, wherein the *Pseudomonas* bacteria is selected from the group consisting of *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802).

7. The method according to claim 5, wherein the composition comprises between about $5.0 \times 10^7$ and $2.0 \times 10^8$ cfu per mL *Pseudomonas* bacteria.

8. The method of claim 5, wherein the fish pathogen is selected from the group consisting of *Flavobacterium columnare*, *Aeromonas salmonicida*, *Streptococcus agalactiae*, *Streptococcus iniae*, *Vibrio parahaemolyticus*, *Saprolegnia parasitica*, and *Tenacibaculum maritimum*.

9. The method according to claim 5, wherein the associated disease is selected from the group consisting of furunculosis, streptococcosis, vibriosis, acute hepatopancreatic necrosis disease, saprolegniasis, and tenacibaculosis.

10. The method according to claim 5, wherein the fish is selected from the group consisting of fresh-water fish and sea-water fish.

11. The method according to claim 5, wherein the fish is selected from the group consisting of wild fish and farm fish.

12. The method according to claim 5, wherein the fish is selected from the group consisting of Salmon, Trout, Cyprinids, Pike, Perch, Bullheads, Turbot, and Halibut.

13. The method according to claim 1, wherein the fish is selected from the group consisting of wild fish and farm fish.

14. The method according to claim 1, wherein the fish is selected from the group consisting of Salmon, Trout, Cyprinids, Pike, Perch, Bullheads, Turbot, and Halibut.

15. The method of claim 1, wherein the composition is produced from a *Pseudomonas soli* or *Pseudomonas mosselii* bacteria is selected from the group consisting of *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802).

16. A method of controlling a pathogen and associated disease of a crustacean or a mollusk comprising the steps of
   (i) producing a composition from *Pseudomonas soli* or *Pseudomonas mosselii* comprising a *Pseudomonas* bacterial metabolite as Formula (I)

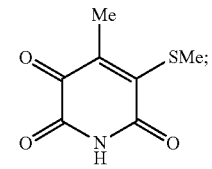

and
   (ii) applying said composition to the crustacean or mollusk to inhibit the growth of the pathogen and the associated disease on the crustacean or mollusk.

17. The method of claim 16, wherein the pathogen is selected from the genera of *Vibrio*.

18. The method according to claim 16, wherein the associated disease is vibriosis, acute hepatopancreatic necrosis disease, or contamination in the crustacean and mollusk.

19. The method according to claim 16, wherein the crustacean is selected from the group consisting of shrimp and crab.

20. The method according to claim 16, wherein the mollusk is selected from the group consisting of oyster, conch, and squid.

21. The method according to claim 16, wherein the *Pseudomonas soli* or *Pseudomonas mosselii* is selected from the group consisting of *Pseudomonas soli* 0617-T307 (Accession No. PTA-126796), *Pseudomonas soli* 0917-T305 (Accession No. PTA-126797), *Pseudomonas soli* 0917-T306 (Accession No. PTA-126798), *Pseudomonas soli* 0917-T307 (Accession No. PTA-126799), *Pseudomonas mosselii* 0118-T319 (Accession No. PTA-126800), *Pseudomonas mosselii* 0318-T327 (Accession No. PTA-126801), and *Pseudomonas mosselii* 0418-T328 (Accession No. PTA-126802).

* * * * *